United States Patent
Nakagawara

(10) Patent No.: US 7,524,291 B1
(45) Date of Patent: Apr. 28, 2009

(54) CUFF-BLOCK FOR FINGER ARTERIAL BLOOD PRESSURE MONITOR

(75) Inventor: Minoru Nakagawara, Tokyo (JP)

(73) Assignee: NEC Medical Systems, Ltd., Tokyo (JP)

( * ) Notice: Subject to any disclaimer, the term of this patent is extended or adjusted under 35 U.S.C. 154(b) by 0 days.

(21) Appl. No.: 09/349,573

(22) Filed: Jul. 8, 1999

(30) Foreign Application Priority Data

Dec. 2, 1998 (JP) .................. P10342807

(51) Int. Cl.
*A61B 5/02* (2006.01)
*A61B 17/00* (2006.01)
(52) U.S. Cl. ...................... 600/499; 606/202
(58) Field of Classification Search ............ 600/485, 600/495
See application file for complete search history.

(56) References Cited

U.S. PATENT DOCUMENTS 4,210,147 A * 7/1980 Nestor et al. ............. 606/202
4,347,852 A * 9/1982 Tan ........................ 600/500
5,035,243 A * 7/1991 Muz ....................... 600/500
5,291,895 A * 3/1994 McIntyre .................. 600/500
5,755,229 A * 5/1998 Amano et al. ............. 600/500
5,807,266 A * 9/1998 Itonaga et al. ............ 600/500

* cited by examiner

*Primary Examiner*—Robert L. Nasser
(74) *Attorney, Agent, or Firm*—Frommer Lawrence & Haug LLP; William S. Frommer

(57) ABSTRACT

A cuff-block for a finger arterial blood pressure monitor is able to relieve a blood flow impediment and the hindrance of a finger motion at the measuring site during the finger arterial blood pressure monitoring.

A disk-like cuff (12) for local pressurization is attached over a finger artery (6) on a proximal finger portion (4) of a measured finger (1), this cuff (12) is held by a cuff-holding portion (11a) of an annular cuff-fixing member (11) put from the tip end portion of the measured finger (1), and the cuff-fixing member (11) is supported on the measured finger (1) with local supportings by forked supporting points (11a, 11b) of the cuff-fixing member (11) placed on respectively portions of a proximal joint (1c) and a medial one (1b).

3 Claims, 3 Drawing Sheets

CUFF-BLOCK FOR FINGER ARTERIAL BLOOD PRESSURE MONITOR

BACKGROUND OF THE INVENTION

1. Field of the Invention

The present invention relates to a cuff-block for measurement of the finger arterial blood pressure using a non-invasive finger arterial blood pressure monitor.

More particularly, this invention relates to a cuff-block for measurement of the finger arterial blood pressure using a cuff for local pressurization and a cuff-fixing member for firmly attaching the cuff to the finger with some locally supports placed on the portion of the finger joints, so that a blood flow impediment and the hindrance to the finger motion due to the non-invasively measurement of finger arterial blood pressure can be relieved.

2. Description of the Prior Art

Heretofore, as a non-invasive finger arterial blood pressure monitor, there have been available three kind of measurement techniques of the cuff-oscillometric method, the volume-oscillometric method and the volume-compensation method.

The cuff-oscillometric method is the technique using a cuff pressure oscillation made by a vascular pulsation under the cuff and the blood pressure is indirectly estimated from the change of this pressure oscillation pattern.

The volume-oscillometric method is the technique for estimating a blood pressure using a photo-plethysmograph which detects a pulsatile component of vascular volume under the cuff.

Further, the volume-compensation method is the technique in which a vascular volume servo-control system instantaneously controls the cuff pressure so as to make the vascular volume to a reference volume which corresponds to an unloaded vascular volume detected by the volume-oscillometric method.

Therefore, the cuff pressure tracks the intra-arterial blood pressure, and the blood pressure can be monitored indirectly by measuring the cuff pressure.

According to the volume-compensation method, there are advantages of beat-by-beat measurement of systolic, mean and diastolic blood pressure as well as of obtaining a blood pressure wave.

A belt-like cuff with an appropriate width, pressure of which is transmitted to the arteries under the cuff via the subcutaneous tissue, has conventionally been applied for the indirect measurement of the finger arterial blood pressure based on any one of these methods mentioned above.

The cuff pressure is continuously set above intra-venous blood pressure which is much below intra-arterial blood pressure, due to the fact that the cuff pressure is controlled within a range from diastolic to systolic blood pressure in order to measure the finger arterial blood pressure using the above mentioned methods.

By the way, concerning the finger vascular system, two arteries run parallel with the phalanges and veins run beneath the dermal tissue with complicated crossings.

Therefore, it causes blood flow impediment and venous congestion under the cuff and its distal portion that a circumferential pressurization by the belt-like cuff occludes the veins under the cuff in order to measure the finger arterial blood pressure.

Moreover, it causes hindrance to the finger motion at the blood pressure measuring site that the pressurization by the belt-like cuff constricts various muscles and tendons concerned the finger motion and obstructs the subcutaneous tissue volume increasing due to the crooking the finger.

SUMMARY OF THE INVENTION

In view of the aforesaid aspect, it is an object of the present invention to provide a cuff-block for measurement of the finger arterial blood pressure using a non-invasive finger arterial blood pressure monitor in which the blood flow impediment and the hindrance to the finger motion due to the non-invasively measurement of finger arterial blood pressure can be relieved.

According to an aspect of the present invention, there is provided a cuff-block for measurement of the finger arterial blood pressure using a non-invasive finger arterial blood pressure monitor.

This cuff-block for the measurement of the finger arterial blood pressure is comprised of a cuff for local pressurization to be attached over a finger artery located at a proximal finger portion or a medial finger portion and a cuff-fixing means for firmly attaching the cuff to the finger with some locally supports.

With the above-mentioned arrangement, it is possible to relieve the blood flow impediment and venous congestion under the cuff and its distal portion, since only some veins located under the cuff and under the portion used by the cuff-fixing means but most of veins are occluded in order to measure the finger arterial blood pressure.

Also, it is possible to relieve the hindrance to the finger motion at the blood pressure measuring site, since the constriction of the muscles and tendons concerned the finger motion and the obstruction of the subcutaneous tissue volume increasing due to the crooking the finger are not produced by the measurement of the finger arterial blood pressure.

DESCRIPTION OF THE PREFERRED EMBODIMENTS

A finger arterial blood pressure monitoring cuff-block according to embodiments of the present invention will hereinafter be described with reference to the drawings.

Figure 1:
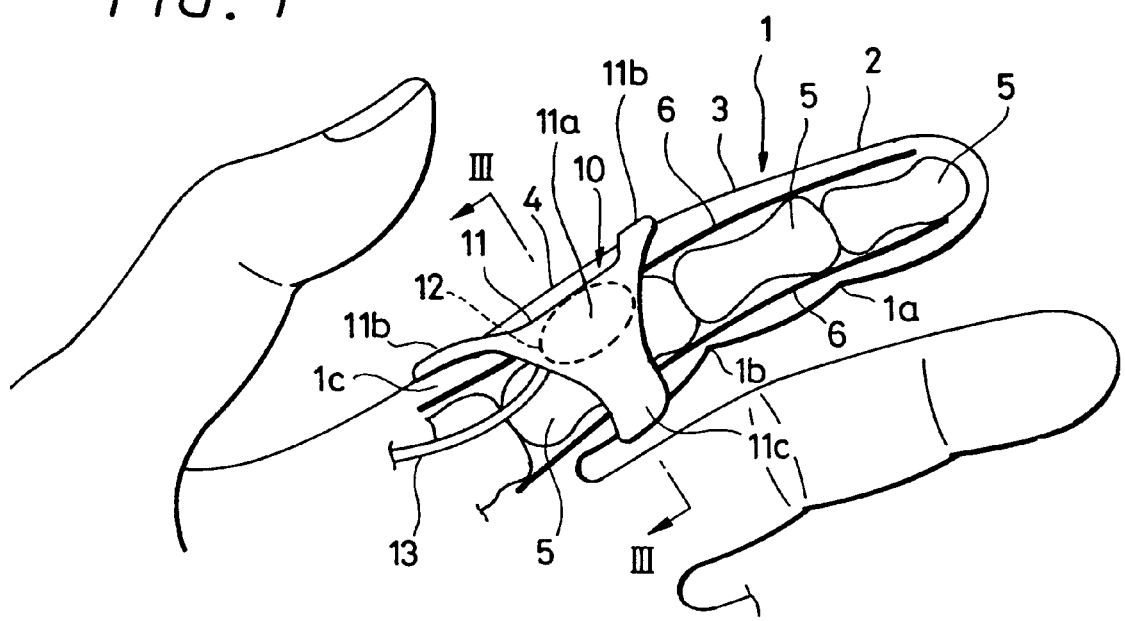
FIG. 1 is a respective view illustrating the manner in which a finger arterial blood pressure monitoring cuff-block according to the present invention is in use when the cuff-block is seen from the palm.

FIG. 1 of the accompanying drawings is a perspective view illustrating the manner in which the finger arterial blood pressure monitoring cuff-block is attached to the hand from the side of the palm of the hand.

Figure 2:
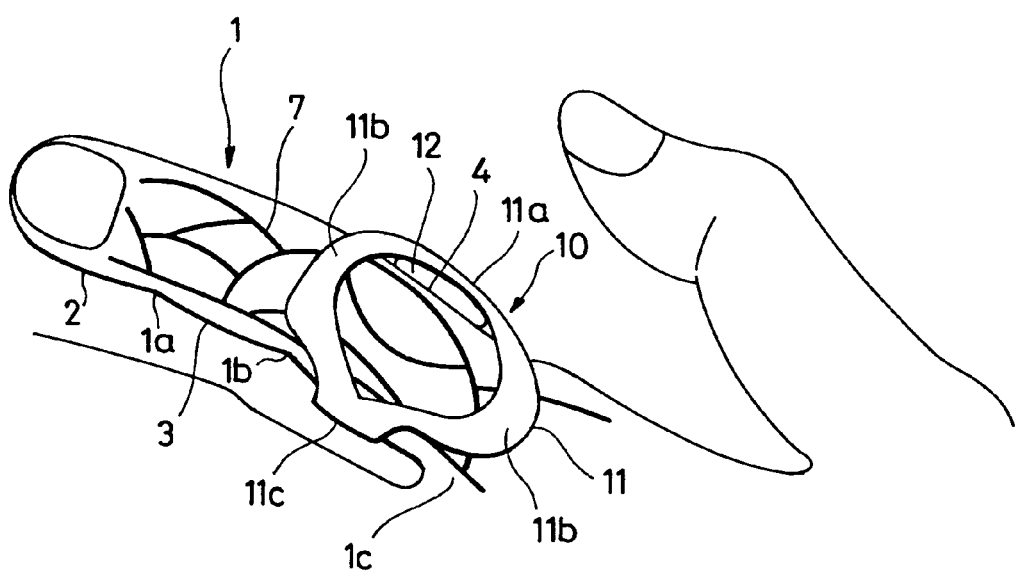
FIG. 2 is a perspective view illustrating the manner in which a finger arterial blood pressure monitoring cuff-block according to the present invention is in use when the cuff-block is seen from the back.

FIG. 2 is a perspective view illustrating the manner in which the finger arterial blood pressure monitoring cuff-block is attached to the hand from the side of the back of the hand.

Figure 3:
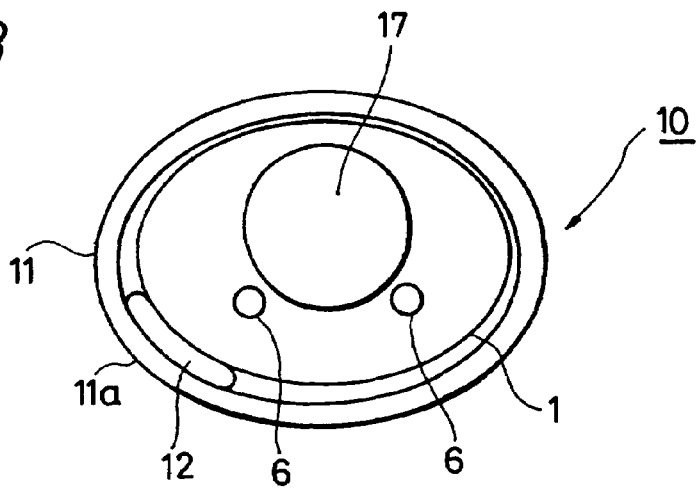
FIG. 3 is a diagram taken along the line III-III in FIG. 1.

FIG. 3 is a diagram taken along the line III-III in FIG. 1.

Figure 4:
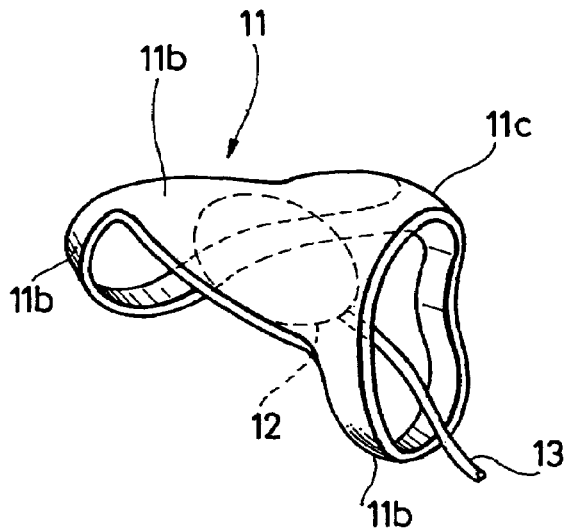
FIG. 4 is a perspective view illustrating a finger arterial blood pressure monitoring cuff-block according to an embodiment of the resent invention.

FIG. 4 is a perspective view illustrating a finger arterial blood pressure monitoring cuff-block according to the embodiment of the present invention.

In this embodiment, there is illustrated an example in which a finger arterial blood pressure monitoring cuff-block is attached to an index finger 1 of the left hand.

The structure, of the index finger 1 will be described below.

The finger tip of a distal joint 1*a* is a distal finger portion 2, a portion between the distal joint 1*a* and a medial joint 1*b* is a medial finger portion 3, and a portion between the medial joint 1*b* and a proximal joint 1*c* is a proximal finger portion 4.

Finger arteries 6, 6 run parallel with the medial and lateral side of phalanges 5 respectively.

Further, finger veins 7 run beneath the dermal tissue of the index finger 1 with complicated crossings as shown in FIG. 2.

A cuff-block, which is generally denoted by reference numeral 10, is attached to the above-mentioned index finger 1 at its proximal finger portion 4.

The finger arterial blood pressure monitoring cuff-block 10 comprises, as shown in FIG. 4, a cuff-fixing member 11 formed of an annular plastic or metal mold product and a cuff 12 which can make the local pressurization, attached firmly over the artery 6 using this cuff-fixing member 11.

The cuff-fixing member 11 has a special shape such that it is branched from a cuff holding portion 11*a* to provide linear forked supporting portions 11*b*, 11*b* which are made as one belt-like portion 11*c* and then integrally joined to the cuff holding portion 11*a* on substantially the opposite side to the supporting portions 11*b*, 11*b*.

On the other hand, the cuff 12 is formed of a mold product of approximately a disk shape the inside of which is hollow made of a rubber material or vinyl material with excellent flexibility. The cuff 12 is connected with a well-known blood pressure measuring instrument (not shown) through a tube 13 to or from which an air or liquid is supplied or evacuated.

The cuff 12 is attached over the finger artery 6 (surface opposing the thumb in that embodiment) in the central portion of the proximal finger portion 4 and held by the cuff holding portion 11*a* of the cuff-fixing member 11.

In that case, the cuff-fixing member 11 is put from the tip end side of the index finger 1 and the cuff holding portion 11*a* covers the one side of the cuff 12, thereby making it possible to hold the cuff 12 over the finger artery 6 at the central portion of the proximal finger portion 4.

In that case, the supporting points of the cuff-fixing member 11 attached to the index finger 1 are three points such that the two supporting portions 11*b*, 11*b* are supported respectively on the back of the medial joint 1*b* (portion of caput proximal phalanx) and the proximal joint 1*c* (portion of basis proximal phalanx) and the other supporting point is the cuff 12 which is attached on the proximal finger portion 4 with holding by the cuff-holding portion 11*a*.

As shown in FIG. 3, there is gently or no contact to the index finger 1 under the cuff-fixing member 11 but the portion of the three points mentioned above.

Moreover, the supporting points of the two supporting portion 11*b*, 11*b* of the cuff-fixing member 11 on the index finger 1 are not limited on the back of the medial joint 1*b* and the proximal joint 1*c*, set around the respective joints.

Thus, when the cuff pressure of the cuff 12 is increased by supplying an air or liquid into the cuff 12, the pressure of the cuff 12 is transmitted to the artery 6 under the cuff 12 via the subcutaneous tissue, thereby making it possible to measure the finger arterial blood pressure.

Since the cuff-block 10 for the finger arterial blood pressure monitor is arranged as described above, the cuff-fixing member 11 provides to support the cuff 12 with some local pressurization points such as the cuff 12 attaching point and two supporting points.

Accordingly, when the finger arterial 6 blood pressure is measured, blood flow of another artery 6 and veins 7 except the veins under the supporting points are not affected from the local pressurization for the monitor.

Also, since the finger veins 7 run with complicated crossings and the finger artery 6 of the measuring site is not continuously occluded, the blood circulation under the cuff 12 and in its distal portion are not impeded, thereby making it possible to avoid the blood flow impediment such as venous congestion during a blood pressure measurement in a long period of time.

Thus, the present invention can be suitably applied to the cuff-block for a finger arterial blood pressure monitor based on the volume-compensation method or the like.

Moreover, since the local pressurization for the blood pressure measurement dose not make the constriction of the muscles and tendons and the obstruction of the subcutaneous tissue volume increasing due to the crooking the finger at the blood pressure measuring site, the subject can move his finger freely.

Furthermore, since the local pressurization for the blood pressure measurement dose not obstruct the subcutaneous tissue volume increasing due to the crooking the finger at the blood pressure measuring site, it is reduced that the influence of the subject's finger motion on the pressure transmission between the cuff 12 and the finger artery 6.

Accordingly, it becomes possible to accurately measure the finger arterial blood pressure without the influence of the subject's finger motion.

Figure 5:
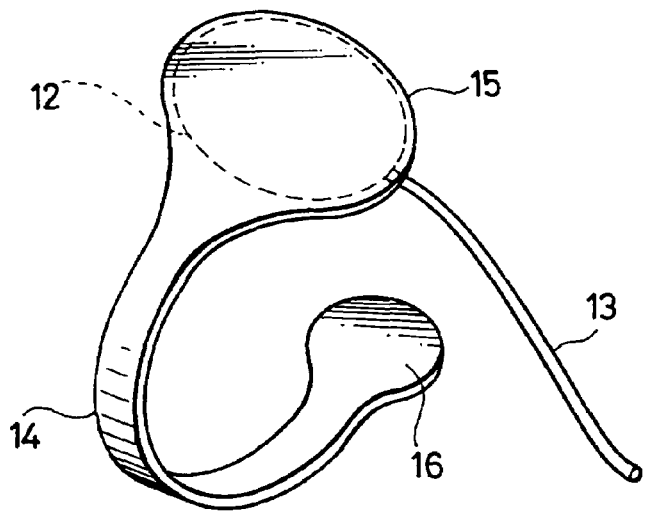
FIG. 5 is a perspective view illustrating a finger arterial blood pressure monitoring cuff-block according to another embodiment of the present invention.

FIG. 5 shows a cuff-block for a finger arterial blood pressure monitor according to another embodiment of the present invention.

According to this embodiment, in FIG. 5, reference numeral 14 depicts a cuff-fixing member which is formed of a flexible or elastic arcuate plastic mold product or metal mold product whose overall shape is substantially U-letter.

One end of this cuff-fixing member 14 is formed as a cuff holding portion 15 which hold the cuff 12 so as to cover the whole of the cuff 12.

The other end of this cuff-fixing member 14 is opposed to the cuff holding portion 15 and is formed as a measured finger supporting portion 16.

The thus arranged cuff-fixing member 14 can be attached to the measured finger such that the cuff 12 attached over the finger artery is held firmly by the cuff holding portion 15 and the measured finger is sandwiched by the cuff holding portion 15 and supporting portion 16.

Since the cuff-fixing member 14 in this case can be supported to the measured finger only at two points, there is only the influence of the local pressurization for the blood pressure measurement on an artery and a part of veins, similarly to the aforementioned cuff-fixing member 11.

Thus, the blood circulation under the cuff 12 and in its distal portion are not impeded.

Therefore, it is possible to avoid the blood flow impediment such as venous congestion during a blood pressure measurement in a long period of time.

Moreover, since the local pressurization for the blood pressure measurement does not make the constriction of the muscles and tendons and the obstruction of the subcutaneous tissue volume increasing due to the crooking the finger at the blood pressure measuring site, the subject can move his finger freely.

The present invention is not limited to the above-mentioned illustrated embodiments, and may be variously modified without departing from the gist of the present invention.

For example, while the cuff 12 is made separately from the cuff-fixing member 11 or the cuff-fixing member 14 each other as described above, the present invention is not limited thereto. And the cuff 12 may be integrally molded on the rear surface of the cuff holding portion 11a or the cuff holding portion 15. According to this modified arrangement, the cuff-block may be easily attached by only positioning the cuff 12 at the measured portion after the cuff-fixing member is attached to the measured finger.

The measured portion of the measured finger is not limited to the proximal finger portion 4, the cuff 12 may be attached to the medial finger portion 3 of the measured finger 1.

Therefore, the measured finger is not limited to the index finger 1, it may be measured at the other finger with measured results similar to those of the above-mentioned cases being achieved.

The fixing points at which the cuff-fixing member is fixed to the measured finger is not limited to the two-point support and the three-point support, and the cuff-fixing member may be attached to the measured finger at many supporting points so long as venous congestion is not caused by the local pressurization for the finger artery blood pressure measurement and the finger motion is not hindered.

Further, since the fingers of men and women are different in size, the cuff-block for finger arterial blood pressure monitor may cope with such cases by either modifying the cuff-fixing member such that the size of the cuff-fixing member may be varied freely or preparing cuff-fixing members of different sizes.

A further example of the cuff-fixing member according to the present invention, in which the size of the cuff-fixing member can be varied freely, will be described with reference to FIG. 6

Figure 6:
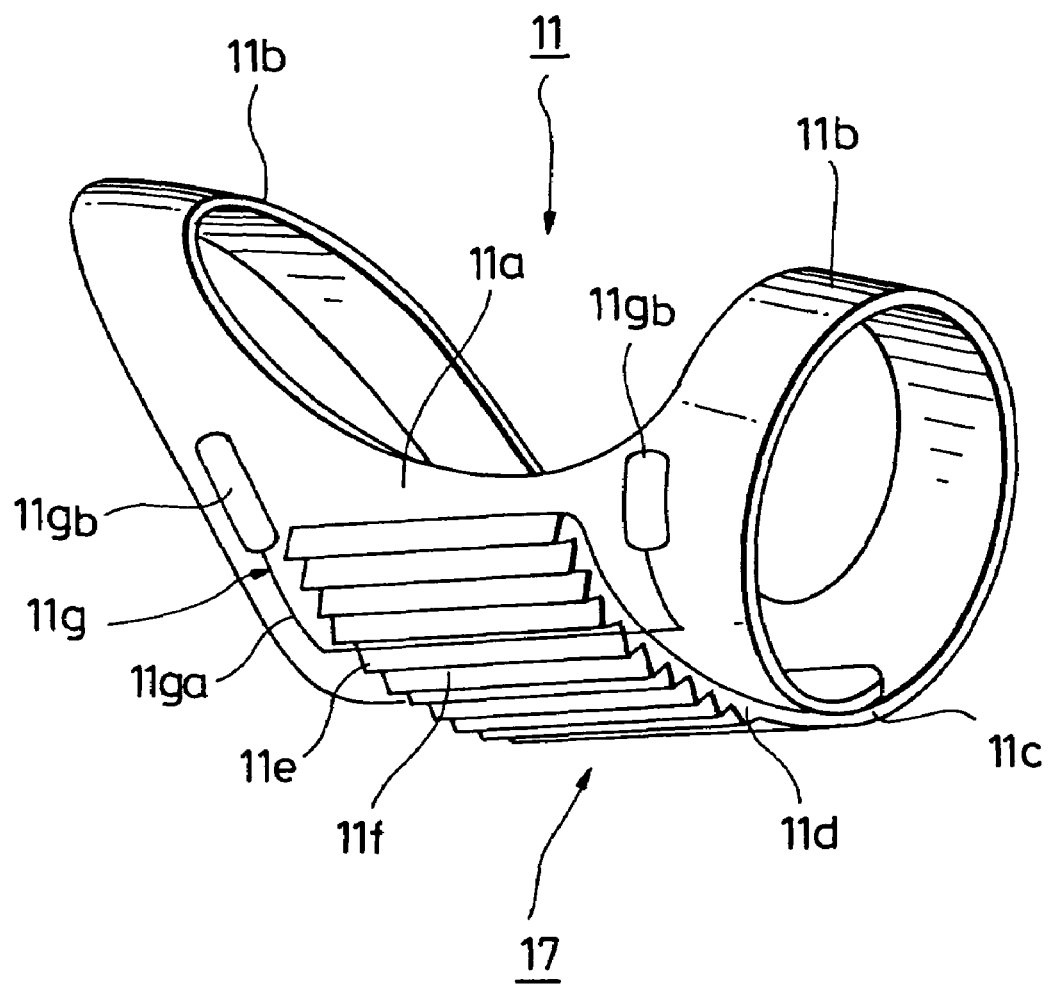
FIG. 6 is a perspective view illustrating a finger arterial blood pressure monitoring cuff-block according to a further embodiment of the present invention.

Since the example show in FIG. 6 is such one that a ratchet mechanism 17 is provided on the cuff-fixing member 11 show in, for example, FIG. 4, the parts of the example in FIG. 6 similar to more in FIG. 4 are marked with the same reference numerals, respectively.

In the example shown in FIG. 6, forked supporting portions 11b, 11b branched from the cuff-holding portion 11a, under which the cuff 12 is fixed though not shown similar to the example shown in FIG. 4, are integrated to provide one belt-like portion 11c and the one belt-like portion 11c is not connected to the cuff-holding portion 11a but is separated therefrom unlike the example shown in FIG. 4.

On the outer surface of a free end portion 11d of the belt-like portion 11c, there is formed a saw-tooth portion 11e composed of a plurality of concave and convex portions which are extended parallel one another in the width direction of the free end portion 11d over a predetermined length in the length direction of free end portion 11d.

Meanwhile, on the outer surface of the cuff-holding portion 11a at its part on which the free end portion 11d will be overlapped upon using, there is formed a stopper 11g to fix the free end portion 11d at a desired position.

That is, the stopper 11g is formed of a wire 11ga, which is made of a material having an elasticity and has a length and a diameter capable of being engaged with any of concave portions 11f of the saw-tooth portion 11e to fixed the free end portion 11d thereat, and of a pair of holding portions 11gb, 11gb, which are each fixed on the outer surface of the cuff-holding portion 11a with a predetermined interval at predetermined positions and fixedly support both ends of the wire 11ga, respectively.

In this way, the ratchet mechanism 17 is formed of the saw-tooth portion 11e and the stopper 11g mainly.

When the cuff-fixing member 11 shown in FIG. 6 is attached to the index finger 1 and fixed thereon as shown in, for example, FIG. 1, it is enough that the free end portion 11d of the left-like portion 11c is released from the stopper 11g to develop the cuff-fixing member 11, the cuff-fixing member 11 thus developed is wound around the index finger 1 similar to that shown in FIG. 1, and then the wire 11ga of the stopper 11g is engaged with a desired concave portion 11f.

In this case, it is needless to say that the ratchet mechanism 17 is not limited to the combination of saw-tooth portion 11e and stopper 11g illustrated in FIG. 6 and takes many modifications and variations.

Further, the annular cuff-fixing member may not always be put from the tip end portion of the measured finger but the cuff-fixing member may be cut a part at its one portion and the cuff-fixing member may be widened from the thus cut portion by utilizing the resilient force of the cuff-fixing member and attached to the measured finger.

As described above, according to the cuff-block for finger arterial blood pressure monitor of the present invention, since the cuff is attached over the finger artery and this cuff is held by the cuff-fixing member with two local supporting points on the measured finger, there is only the influence of the local pressurization for the blood pressure measurement on an artery and two supporting portions of veins, similarly to the aforementioned cuff-fixing member 11, the blood circulation under the cuff 12 and in its distal portion are not impeded, and it is possible to avoid the blood flow impediment such as venous congestion during a blood pressure measurement in a long period of time.

Thus, the present invention is extremely suitable for use in a cuff-block for a finger arterial blood pressure monitor based on the volume-compensation method.

Further, since the local pressurization for the blood pressure measurement does not make the constriction of the muscles and tendons and the obstruction of the subcutaneous tissue volume increasing due to the crooking the finger at the blood pressure measuring site, the subject can move his finger freely.

Furthermore, since the local pressurization for the blood pressure measurement dose not obstruct the subcutaneous tissue volume increasing due to the crooking the finger at the blood pressure measuring site, it is reduced that the influence of the subject's finger motion on the pressure transmission between the cuff and the measured finger artery.

Accordingly, it becomes possible to accurately measure the finger arterial blood pressure without the influence of the subjects finger motion.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A cuff-block for the non-invasive sensing within a finger of arterial blood pressure, comprising:
   a cuff adapted to be placed over a proximal or a medial finger portion of an artery in the finger; and
   means for holding said cuff on said finger such that the cuff is supported on said finger at a plurality of discrete portions remote from said artery, said holding means comprising a cuff-holding portion, two forked supporting portions each extended from said cuff-holding, a belt-like portion formed by integrating the free ends of said forked supporting portions, and a ratchet mechanism provided in connection with a free end support of said belt-like portion and an outer surface of said cuff-holding portion.

2. The cuff-block as claimed in claim 1, wherein said ratchet mechanism comprises a saw-tooth portion formed on an outer surface of said free end portion of said belt-like portion and a stopper formed on the outer surface of said cuff-holding portion.

3. The cuff-block as claimed in claim 2, wherein said saw-tooth portion comprises a plurality of concave and convex portions extended parallel to one another in a width direction of said free end portion of said belt-like portion, and said stopper is comprised of a wire and holding portions for fixedly holding both end of said wire, said wire being capable of being engaged with any one of said concave portions.

* * * * *